(12) United States Patent
Ackerson et al.

(10) Patent No.: US 10,961,463 B2
(45) Date of Patent: *Mar. 30, 2021

(54) PROCESS FOR HYDROPROCESSING OF NON-PETROLEUM FEEDSTOCKS

(71) Applicant: Duke Technologies, LLC, Fayetteville, AR (US)

(72) Inventors: Michael D. Ackerson, Elkins, AR (US); Michael Steven Byars, Fayetteville, AR (US)

(73) Assignee: Duke Technologies, LLC, Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,602

(22) Filed: Nov. 25, 2019

(65) Prior Publication Data

US 2020/0087577 A1    Mar. 19, 2020

Related U.S. Application Data

(63) Continuation of application No. 15/818,177, filed on Nov. 20, 2017, now Pat. No. 10,487,268, which is a
(Continued)

(51) Int. Cl.
*C10G 3/00* (2006.01)
*C07C 1/04* (2006.01)
*C10G 49/00* (2006.01)

(52) U.S. Cl.
CPC ............... *C10G 3/42* (2013.01); *C10G 3/50* (2013.01); *C10G 49/00* (2013.01); *C07C 1/0485* (2013.01);
(Continued)

(58) Field of Classification Search
USPC ......................................... 585/240–242, 357
See application file for complete search history.

(56) References Cited

U.S. PATENT DOCUMENTS 2,646,387 A  7/1953  Francis
2,698,279 A  12/1954  Mondria
(Continued)

FOREIGN PATENT DOCUMENTS

EP  0419123 A  3/1991
EP  0464931 A1  1/1992
(Continued)

OTHER PUBLICATIONS

B.M. Sankey and D.A. Gudelis, 18.3 Lube Oil Extraction, Imperial Research Dept. Canada, admitted prior art.
(Continued)

*Primary Examiner* — Nina Bhat
(74) *Attorney, Agent, or Firm* — Grady K. Bergen; Griggs Bergen LLP

(57) ABSTRACT

A method of hydroprocessing is performed wherein non-petroleum feedstocks, such as those containing from about 10% or more olefinic compounds or heteroatom contaminants by weight, are treated in a first reaction zone to provide reaction products. The process involves introducing the feedstock along with diluents or a recycle and hydrogen in a first reaction zone and allowing the feed and hydrogen to react in a liquid phase within the first reaction zone to produce reaction products. The reaction products are cooled and/or water is removed from the reaction products. At least a portion of the cooled and/or separated reaction product are introduced as a feed along with hydrogen into a second reaction zone containing a hydroprocessing catalyst. The feed and hydrogen are allowed to react in a liquid phase within the second reaction zone to produce a second-reaction-zone reaction product.

20 Claims, 4 Drawing Sheets

Related U.S. Application Data continuation of application No. 14/816,404, filed on Aug. 3, 2015, now Pat. No. 9,828,552, which is a continuation of application No. 13/353,856, filed on Jan. 19, 2012, now Pat. No. 9,096,804.

(60) Provisional application No. 61/434,414, filed on Jan. 19, 2011.

(52) U.S. Cl.
CPC .............. *C10G 2300/1014* (2013.01); *C10G 2300/1018* (2013.01); *C10G 2300/202* (2013.01); *C10G 2300/4081* (2013.01); *C10G 2300/802* (2013.01); *Y02P 30/20* (2015.11)

(56) References Cited

U.S. PATENT DOCUMENTS

| | | |
|---|---|---|
| 2,966,456 A | 12/1960 | Honeycutt |
| 3,152,981 A | 10/1964 | Berlin et al. |
| 3,730,880 A | 5/1973 | Van der Toorn et al. |
| 3,880,598 A | 4/1975 | Van der Toorn et al. |
| 3,958,957 A | 5/1976 | Koh et al. |
| 4,011,884 A | 3/1977 | Drori |
| 4,030,521 A | 6/1977 | Karlsson |
| 4,047,655 A | 9/1977 | McCafferty |
| 4,209,381 A | 6/1980 | Kelly, Jr. |
| 4,311,578 A | 1/1982 | Fant et al. |
| 4,333,824 A | 6/1982 | Brown et al. |
| 4,381,234 A | 4/1983 | Audeh et al. |
| 4,390,411 A | 6/1983 | Scinta et al. |
| 4,397,736 A | 8/1983 | Low |
| 4,399,025 A | 8/1983 | Fletcher et al. |
| 4,404,809 A | 9/1983 | Johnson et al. |
| 4,424,110 A | 1/1984 | Bearden, Jr. et al. |
| 4,428,821 A | 1/1984 | Baset |
| 4,441,983 A | 4/1984 | Garg |
| 4,464,245 A | 8/1984 | Hodek |
| 4,485,004 A | 11/1984 | Fisher et al. |
| 4,486,293 A | 12/1984 | Garg |
| 4,491,511 A | 1/1985 | Skinner et al. |
| 4,514,282 A | 1/1985 | Skinner et al. |
| 4,536,275 A | 8/1985 | Bronfenbrenner et al. |
| RE32,120 E | 4/1986 | Low |
| 4,585,546 A | 4/1986 | Bowes et al. |
| 4,591,426 A | 5/1986 | Krasuk et al. |
| 4,663,056 A | 5/1987 | Ditman |
| 4,678,556 A | 7/1987 | Hicks et al. |
| 4,698,147 A | 10/1987 | McConaghy, Jr. |
| 4,715,398 A | 12/1987 | Shouldice et al. |
| 4,761,513 A | 8/1988 | Steacy |
| 4,772,157 A | 9/1988 | Obermeyer |
| 4,844,117 A | 7/1989 | Sung |
| 4,853,104 A | 8/1989 | Degnan, Jr. et al. |
| 4,857,168 A | 8/1989 | Kubo et al. |
| 4,880,449 A | 11/1989 | Babyak |
| 4,909,927 A | 3/1990 | Bell |
| 4,911,821 A | 3/1990 | Katzer et al. |
| 4,917,135 A | 4/1990 | Duncan |
| 4,944,863 A | 7/1990 | Smith et al. |
| 4,968,409 A | 11/1990 | Smith |
| 4,970,190 A | 11/1990 | Lopez et al. |
| 4,995,961 A | 2/1991 | Hays et al. |
| 5,009,770 A | 4/1991 | Miller et al. |
| 5,013,424 A | 5/1991 | James, Jr. et al. |
| 5,021,142 A | 6/1991 | Bortz et al. |
| 5,024,750 A | 6/1991 | Sughrue, II et al. |
| 5,035,793 A | 7/1991 | Nebesh et al. |
| 5,068,025 A | 11/1991 | Bhan |
| 5,071,540 A | 12/1991 | Culross et al. |
| 5,098,452 A | 3/1992 | Feller |
| 5,132,007 A | 3/1992 | Meyer et al. |
| 5,110,445 A | 5/1992 | Chen et al. |
| 5,110,450 A | 5/1992 | Culross et al. |
| 5,120,426 A | 6/1992 | Johnston et al. |
| 5,164,074 A | 11/1992 | Houghton |
| 5,178,750 A | 1/1993 | Mead |
| 5,180,868 A | 1/1993 | Baker et al. |
| 5,183,556 A | 2/1993 | Reilly et al. |
| 5,196,116 A | 3/1993 | Ackerson et al. |
| 5,198,103 A | 3/1993 | Meyer et al. |
| 5,227,552 A | 7/1993 | Chang et al. |
| 5,240,592 A | 8/1993 | Meyer et al. |
| 5,269,910 A | 12/1993 | Matsumura et al. |
| 5,312,543 A | 5/1994 | Taylor et al. |
| 5,336,395 A | 8/1994 | Pabst et al. |
| 5,379,795 A | 1/1995 | Hartley et al. |
| 5,395,511 A | 3/1995 | Kubo et al. |
| 5,474,668 A | 12/1995 | Ackerson et al. |
| 5,496,464 A | 3/1996 | Piskorz et al. |
| 5,589,057 A | 12/1996 | Trimble et al. |
| 5,620,588 A | 4/1997 | Ackerson et al. |
| 5,655,232 A | 8/1997 | Buckwalter |
| 5,671,603 A | 9/1997 | McCorkle et al. |
| 5,705,052 A | 1/1998 | Gupta |
| 5,714,662 A | 2/1998 | Vora et al. |
| 5,741,414 A | 4/1998 | Waku et al. |
| 5,744,025 A | 4/1998 | Boon et al. |
| 5,817,906 A | 10/1998 | Marker et al. |
| 5,820,749 A | 10/1998 | Haluska et al. |
| 5,827,421 A | 10/1998 | Sherwood, Jr. |
| 5,856,261 A | 1/1999 | Culross et al. |
| 5,868,921 A | 2/1999 | Barre et al. |
| 5,881,753 A | 3/1999 | Bowling |
| 5,906,731 A | 5/1999 | Abdo et al. |
| 5,925,239 A | 7/1999 | Klein et al. |
| 5,928,499 A | 7/1999 | Sherwood, Jr. et al. |
| 5,935,416 A | 8/1999 | Cody et al. |
| 5,954,945 A | 9/1999 | Cayton et al. |
| 5,958,218 A | 9/1999 | Hunter et al. |
| 5,958,220 A | 9/1999 | Reynolds et al. |
| 5,968,348 A | 10/1999 | Sherwood, Jr. |
| 5,972,202 A | 10/1999 | Benham et al. |
| 5,976,353 A | 11/1999 | Cody et al. |
| 6,017,443 A * | 1/2000 | Buchanan .............. C10G 65/04 208/210 |
| 6,123,835 A | 9/2000 | Ackerson et al. |
| 6,299,759 B1 | 10/2001 | Bradway et al. |
| 6,311,711 B1 | 11/2001 | Skoglund |
| 6,428,686 B1 | 8/2002 | Ackerson et al. |
| 6,689,273 B1 | 2/2004 | Kalnes et al. |
| 6,881,326 B2 | 4/2005 | Ackerson et al. |
| 7,291,257 B2 * | 11/2007 | Ackerson .............. C10G 45/22 208/210 |
| 7,300,567 B2 | 11/2007 | Breivik et al. |
| 7,569,136 B2 * | 8/2009 | Ackerson .............. C10G 45/16 208/108 |
| 7,781,629 B2 | 8/2010 | Marchand et al. |
| 9,096,804 B2 * | 8/2015 | Ackerson ................ C10G 3/42 |
| 9,828,552 B1 * | 11/2017 | Ackerson ................ C10G 3/50 |
| 10,487,268 B2 * | 11/2019 | Ackerson ................ C10G 3/42 |
| 2006/0070918 A1 | 4/2006 | Seapan et al. |
| 2008/0173570 A1 | 7/2008 | Marchand et al. |
| 2009/0107033 A1 | 4/2009 | Gudde et al. |
| 2009/0253948 A1 * | 10/2009 | McCall .................... C10G 3/50 585/240 |
| 2009/0253958 A1 | 10/2009 | Ito et al. |
| 2010/0038284 A1 * | 2/2010 | Vergel .................... B01J 8/0488 208/89 |
| 2010/0133144 A1 | 6/2010 | Kokayeff et al. |
| 2010/0137662 A1 | 6/2010 | Sechrist et al. |

FOREIGN PATENT DOCUMENTS

| | | |
|---|---|---|
| EP | 0699733 A1 | 3/1995 |
| FR | 785974 | 5/1935 |
| GB | 934907 | 7/1961 |
| GB | 1232173 | 11/1969 |

(56) References Cited

FOREIGN PATENT DOCUMENTS

GB  1346265 A  2/1974
GB  1407794 A  9/1975

OTHER PUBLICATIONS

J.D. Bushnell and R.J. Fiocco, Engineering Aspects of the Exol N Lube Extraction Process, New Technology in Lube Oil Manufacturing, pp. 159-167, admitted prior art.
L.C. Kemp, Jr., G.B. Hamilton and H.H. Gross, Furfural as a Selective Solvent in Petroleum Refining, Industrial and Engineering Chemistry, Feb. 1948, pp. 220-227, vol. 40, No. 2.
International Search Report and Written Opinion of ISA in counterpart International Application No. PCT/US2012/021890, dated Mar. 7, 2014, pp. 1-22.
International Preliminary Report on Patentability in counterpart International Application No. PCT/US2012/021890, dated Apr. 3, 2014, pp. 1-19.

* cited by examiner

PROCESS FOR HYDROPROCESSING OF NON-PETROLEUM FEEDSTOCKS

CROSS-REFERENCE TO RELATED APPLICATIONS

This application is continuation of U.S. patent application Ser. No. 15/818,177, filed Nov. 20, 2017, now U.S. Pat. No. 10,487,268, issued Nov. 26, 2019, which is a continuation of U.S. patent application Ser. No. 14/816,404, filed Aug. 3, 2015, now U.S. Pat. No. 9,828,552, issued Nov. 28, 2017, which is a continuation of U.S. patent application Ser. No. 13/353,856, filed Jan. 19, 2012, now U.S. Pat. No. 9,096,804, issued Aug. 4, 2015, which claims the benefit of U.S. Provisional Application No. 61/434,414, filed Jan. 19, 2011, each of which is incorporated herein by reference in its entirety for all purposes.

BACKGROUND

In conventional hydroprocessing of petroleum products it is necessary to transfer hydrogen from a vapor phase into the liquid phase where it will be available to react with a petroleum molecule at the surface of the catalyst. This is accomplished by circulating very large volumes of hydrogen gas and the petroleum oil through a catalyst bed. The petroleum oil feed and the hydrogen flow through the catalyst bed and the hydrogen is absorbed into a thin film of oil that is distributed over the catalyst. Because the amount of hydrogen required can be large, e.g. 1000 to 5000 SCF/bbl of liquid, the reactors are very large and can operate at severe conditions, from a few hundred psi to as much as 5000 psi, and temperatures from around 250° F.-900° F.

The temperature inside the reactor is difficult to control in conventional systems. While the temperature of the oil and hydrogen feed introduced into the reaction zone can be controlled, once the feed/hydrogen mixture is inside the reaction zone no adjustments to the system can be made to raise or lower the temperature of the oil/hydrogen mixture. Any changes in the reaction zone temperature must be accomplished through an outside source. As a result, conventional systems often inject cold hydrogen gas into the reaction zone if it becomes too hot. This method of cooling a reactor is expensive and is a potential safety risk.

While controlling the temperature of the reaction zone is often a difficult task in conventional systems, controlling the pressure of the hydroprocessing system is a much easier task. Pressure control systems are used to monitor the pressure of the system. The controls are used to release pressure through a valve or valves if the pressure becomes too great, and to increase the pressure of the system if the pressure becomes too low. A pressure control system cannot be used to control the pressure on a single hydroprocessing reactor, however. This is of no serious consequence, however, because pressure may be maintained on the entire system, but not on individual reactors.

One of the biggest problems with hydroprocessing is catalyst coking. Coking occurs when hydrocarbon molecules become too hot in an environment where the amount of hydrogen available for reaction is insufficient. The hydrocarbon molecules within the reactor crack to the point where coke, a carbonaceous residue, is formed. Cracking can take place on the surface of the catalyst, leading to coke formation and deactivation of the catalyst.

High-contaminant and/or high-olefinic feedstocks further complicate the hydroprocessing process. High-contaminant and/or high-olefinic feedstocks may include petroleum materials but primarily include non-petroleum products, such as renewable feedstocks derived from biological sources. These may be based on vegetable- or animal-derived materials, such as vegetable and animal oils. Such high-contaminant and/or high-olefinic feedstocks may also include pyrolysis oils derived from biomass materials, such as cellulosic biomass materials, or coal. These non-petroleum feedstocks may be highly olefinic and/or contain high levels of heteroatom contaminants, such as oxygen, nitrogen, sulfur, etc. Such olefinic compounds and heteroatom contaminants may be at levels of from about 10% by weight or more of the feed.

In order to produce a valuable product from such highly olefinic and highly contaminated feedstocks, a large amount of hydrogen is required, roughly 1500-4000 scf/bbl. Furthermore, these reactions are highly exothermic. They generate a great deal of heat, significantly more than what is found in a typical hydroprocessing process of petroleum products. The excessive amounts of heat generated put the entire process at great risk. One concern is the effect of such large quantities of heat on the catalyst. It is widely known that overheating, and subsequent coking, is one of the most common causes of catalyst deactivation. In a process that generates significantly more heat than the typical hydroprocessing process, temperature control in order to maintain catalyst activity is crucial. The most serious threat involved in the hydroprocessing of high-contaminant and/or high-olefinic feedstocks, however, is the risk of creating a runaway reaction, a reaction that generates so much heat that the process can no longer be brought under control. Despite turning off heaters and maximizing all cooling efforts, a runaway reaction can continue to heat and has the potential to cause serious damage to the reactor and process equipment. Runaway reactions contribute to a significant number of refinery explosions, damaging equipment, slowing or stopping production, and endangering workers. Consequently, the heat generated by the hydroprocessing of high-contaminant and/or high-olefinic feedstocks is one the greatest problems that must be surmounted.

An additional concern that is unique for high-contaminant feedstocks is the effect of hydroprocessing byproducts on the system. Water, hydrogen sulfide, ammonia, sulfur, carbon, and nitrogen oxides are all common byproducts created during hydroprocessing reactions. While these byproducts are undesirable in the finished product and must eventually be removed from the finished product, when using conventional petroleum feedstocks, these byproducts are not generally present in amounts significant enough to pose any real threat to the integrity of the process. This is not true for high-contaminant feedstocks. The hydroprocessing of these feedstocks results in much larger quantities of these byproducts being present in the system. These byproducts, particularly water, can be especially harmful to the catalyst. If water is allowed to build up in the catalyst bed, a separate aqueous phase can form. This aqueous phase is extremely harmful to the catalyst, essentially causing it to dissolve inside the reactor. In addition, hydrogen sulfide and ammonia, in large quantities, are widely known to inhibit catalyst activity. Therefore, it is of great importance that the quantities of these byproducts created during the hydroprocessing of high-contaminant feedstocks be controlled to prevent or minimize any damage they may cause to the system.

Because prior art methods do not adequately address the problems associated with hydroprocessing highly contaminated and/or highly olefinic feedstocks, improvements are needed.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

Figure 1:
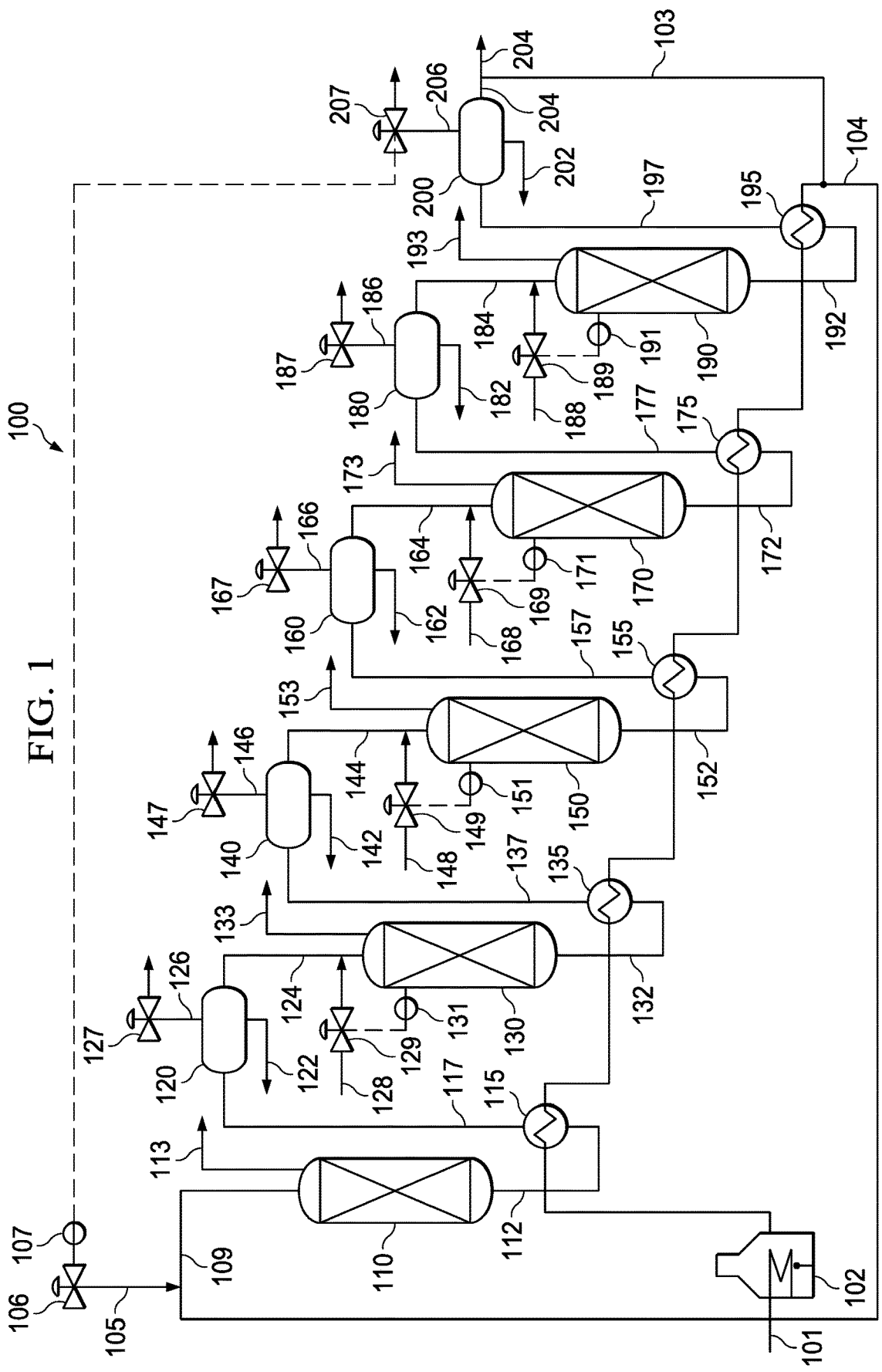
FIG. 1 is a process flow diagram schematic showing a hydroprocessing system that may be used for hydroprocessing high-contaminant and/or high-olefinic feedstocks.

In accordance with the present invention, a process has been developed wherein high-contaminant feedstocks or feedstocks with high-olefinic content can be treated. As used herein, high-contaminant feed stocks are those containing heteroatoms, such as sulfur, nitrogen, oxygen, and metals, which may be at levels of from 10% or more by weight of the feed. High-olefinic feedstocks are those having from 10% or more of olefinic molecules by weight of the feed. Such feedstocks can be converted, through hydroprocessing, into useful products while keeping reaction zone temperatures well-controlled and maintaining catalyst activity. As used herein, the term "hydroprocessing" is meant to include hydrotreating, hydrofinishing, hydrorefining, hydrocracking, hydroisomerization, and hydrodemetalization.

Such high-contaminant and/or high-olefinic feedstocks may include non-petroleum products, such as renewable feedstocks derived from biological sources. These may be derived from or based on vegetable, animal, and cellulosic materials, and combinations of such materials. Such high-contaminant and/or high-olefinic feedstocks may include vegetable oils, animal oils, and other bio oils. The high-contaminant and/or high-olefinic feedstocks may also include pyrolysis oils from biomass materials, such as cellulosic biomass materials, or coal. These feedstocks may be highly olefinic and/or contain heteroatoms, such as oxygen, nitrogen, sulfur, metals, etc. As used herein, with respect to olefinic compounds weight percentages are based on weight of the olefinic molecules. With respect to heteroatom contaminants, weight percentages are based upon the weight of the heteroatoms. Such olefinic compounds and heteroatom contaminants may be at levels of from about 10%, 15%, 20%, 25%, 30%, 35%, 40%, 45%, 50% or more by weight or more of the feedstock. In particular, the olefinic compounds and heteroatom contaminants may make up from about 10% to about 50% by weight of the feedstock. In certain embodiments, the feed stock may have an oxygen content of from about 10%, 15%, 20%, 25%, 30%, 35%, 40%, 45%, 50% by weight or more.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

The high-contaminant and/or high-olefinic feedstock may be entirely a non-petroleum product or material and be treated in accordance with the invention without the addition or combining with any petroleum feedstocks that are treated. In most instances, the high-contaminant and/or high-olefinic feedstock is a renewable material that is derived from biological sources and may also include pyrolysis oils from biomass materials, such as cellulosic biomass materials, or coal. While coal is not generally considered a renewable material, it is a non-petroleum material and for purposes of the present discussion is meant to be included with renewable and biomass materials because of its similar properties and should be construed as such unless otherwise stated or is apparent from its context.

The high-contaminant and/or high-olefinic feedstock may be introduced into a reactor along with hydrogen gas under conditions so that substantially all the feed and hydrogen introduced may be in a continuous liquid phase as a hydrogen-gas-free liquid feed stream prior to introduction into the reactor. This may be accomplished by the use of a diluent that is combined with the feed and hydrogen, as well as setting of the reactor conditions so that all of the hydrogen required in the hydroprocessing reactions is available in solution. The use of such methods wherein in a liquid diluent is used to dissolve hydrogen gas so that it is present in solution for reaction is described in U.S. Pat. Nos. 6,123,835; 6,428,686; 6,881,326; 7,291,257; and 7,569,136, each of which is incorporated herein by reference for all purposes.

The feedstock and hydrogen can then be fed as a liquid to a reactor, such as a plug flow or tubular reactor, packed with hydroprocessing catalyst where the oil and hydrogen react. The reactor may contain no hydrogen gas. In other cases there may be small amounts of hydrogen gas that may be present in the reactor that evolve from solution or that may otherwise be present or introduced into the reactor. In such cases, the reactor may contain from about 10%, 5%, 4%, 3%, 2%, 1% or less of any hydrogen gas by total volume of the reactor. This hydrogen gas within the reactor may eventually enter into solution as the hydrogen in solution is consumed during the reaction. Such hydrogen gas, as well as any other gases (e.g. light end hydrocarbons), may also be vented from the reactor, if desired. In certain embodiments, no hydrogen gas may be added directly to the reactor, with all hydrogen for reaction being mixed with the feed and any diluent prior to introduction into the reactor. In many cases, no additional hydrogen is required to be added, therefore, hydrogen recirculation is avoided, as in trickle bed reactors. The large trickle bed reactors used in conventional hydroprocessing systems can therefore be replaced by much smaller reactors. Elimination of the recycle compressor and the use of, for example plug flow or tubular reactors, may greatly reduce the capital cost of the hydrotreating process. The continuous liquid phase reactors also provide more control over the reaction zone temperature, acting as a heat sink to stabilize the temperature inside the reaction zone. The added diluent also serves to increase the quantity of hydrogen capable of being dissolved into the feedstock and also serves to aid in maintaining a single liquid phase inside the reaction zone.

In other embodiments, the high-contaminant and/or high-olefinic feedstock may be introduced as a liquid phase that contains a quantity of hydrogen gas contained in the liquid, with or without any additional diluents. Such quantities of hydrogen gas in the liquid feed may be small, such as from about 1% to about 15% by volume of the feed. The hydrogen gas may be entrained in the liquid feed without separation of the hydrogen gas prior to being introduced into the reactor. Such excess hydrogen gas may be used as make up as hydrogen is consumed during the reaction. Furthermore, such hydrogen gas may remain in the reactor without venting of excess hydrogen gas from the reactor. If venting of hydrogen gas does occur, it may be vented without facilitating the control of any liquid level within the reactor.

In certain embodiments, hydrogen gas may be present in the reactor in amounts of from greater than 10% to about 60% of hydrogen gas by volume of the reactor, more particularly from greater than 10%, 15%, 20%, 25%, 30%, 35%, 40%, 45%, 50%, or 55% to about 60% by volume of the reactor. Such hydrogen gas within the reactor may be that that is added directly with the feed, without adding hydrogen gas directly into the reactor. Hydrogen gas may be added directly to the reactor in some embodiments, however.

The reactors for hydroprocessing as described herein contain a hydroprocessing catalyst. Such hydroprocessing catalysts are well known in the art. The amount of catalyst used in the reactors may be that that provides sufficient conversion. The amount of catalyst may provide a LHSV of from about 0.1 to about 10 $hr^{-1}$. Reactor temperatures typically range from about 100 to about 500° C.

In the case of a feedstock with high oxygen content, as in, for example, a renewable feedstock such as animal or vegetable oil, etc., the oxygen, under hydroprocessing conditions inside the reaction zone, is converted into water. The greater the quantity of water produced, the more likely it is that two distinct liquid phases will form inside the reaction zone: a hydrocarbon phase and an aqueous phase. If an aqueous liquid phase forms inside the reaction zone, severe damage to the catalyst may result. To maintain catalyst activity, the water created during the reaction between hydrogen and oxygen must be held in solution with the hydrocarbon component and dissolved hydrogen. A diluent or recycle stream added to the feed may provide a greater capacity for holding hydrogen in solution. The diluent or recycle also facilitates adjusting the capacity for holding water in solution, without creating an aqueous phase. In many cases diluent is provided by a product stream of the hydroprocessing reaction that is recycled and added as a diluent. In other cases, such as during startup, diluent may be added from an existing or previously provided diluent source. As used herein, the term "diluent" may therefore be construed as diluent provided as a separate source or as a recycle stream from the process, unless expressly stated otherwise or is apparent from its context. With more diluent or recycle, higher amounts of water, as well as other byproducts, may be held in solution. The diluent or recycle may also serve to stabilize reaction zone temperatures and increases the capacity of the liquids inside the reaction zone for holding heat, dissolved hydrogen, and reaction by-products.

Though the diluent is effective in controlling reaction zone temperatures and mitigating the effects of reaction by-products in hydroprocessing systems utilizing traditional feedstocks, the enormous quantities of heat and reaction by-products produced by a system involved in the hydro-processing of high-contaminant and/or high-olefinic feedstocks may not be managed solely through the addition of a diluent or recycle. To overcome such shortcomings, multiple reactors, or multiple reaction zones, may be used. This allows for the removal of heat and reaction by-products, if necessary or desired, in between reactors and/or reaction zones. Heat can be removed from the effluent between reaction zones by cooling the reaction zone effluent. Reaction by-products can be removed by forming a liquid phase and a gas phase from the cooled reaction products, and removing the gas phase ahead of the next reaction zone. Alternately, the reaction zone effluent can be flashed without any previous cooling step, removing a portion of the reaction by-products and dissipating a great deal of heat with the flash. The removal of additional heat and reaction by-products between reaction zones, in combination with the benefits inside the reactor(s) of operating in a liquid phase and using a liquid diluent or liquid recycle, creates a process that can be safely and efficiently manage highly exothermic reactions and large amounts of catalyst-deactivating reaction by-products, such as those from high-contaminant and/or high-olefinic feeds, without reducing conversion rates.

The process wherein high-contaminant and/or high-olefinic feedstocks are converted through hydroprocessing into useful products keeps reaction zone temperatures well-controlled and maintains catalyst activity. This is accomplished by utilizing the methods described herein to stabilize the temperature of liquids inside the reaction zone, to dissipate heat from reaction zone effluents prior to entering subsequent reaction zones, to minimize the effects of reaction by-products on catalyst beds inside reaction zones, and to remove harmful reaction by-products between reaction zones. The temperature of the liquids inside the reaction zone is stabilized, at least in part, by creating a liquid phase solution inside the reaction zone. This is accomplished by mixing and/or flashing the hydrogen and the feed to be treated in the presence of a diluent having a relatively high solubility for hydrogen. Excess hydrogen may be mixed and/or flashed into the hydrocarbon feed to be treated and diluent solution so that the maximum capacity of the feed and diluent solution for hydrogen is utilized, with or without any amounts of hydrogen gas entrained in such liquid.

The type and amount of diluent added, as well as the reaction zone conditions, can be set so that all of the hydrogen required in the hydroprocessing reaction is available in solution. The feed to be treated, diluent, and hydrogen solution can then be fed to a plug flow, tubular or other reactor packed with catalyst where the feed and hydrogen react.

The reactors may be altered in configuration and in number to accommodate the specifications required of the product, given a specific feed. To achieve the desired product specifications from a particularly contaminated feed may necessitate the addition of one or more additional reactors and/or reaction zones. Even in the case where multiple reactors, or reaction zones, are required, the reactors of the present invention are preferred to conventional reactors because their smaller size and more simple design may result in a reduction of capital cost when compared to conventional systems. In addition to utilizing multiple reactors, it may also be possible to house multiple catalyst beds and reaction zones within a single reactor housing. The creation of multiple-bed reactors further lowers capital cost by utilizing a single reactor vessel to house multiple catalyst beds. The catalyst beds may contain the same catalyst type, or they may contain different catalyst types to more efficiently accomplish the product specification goal.

Most of the reactions that take place in hydroprocessing are highly exothermic, and as a result, a great deal of heat is generated in the reaction zone. The temperature of the reaction zone can be controlled by using a recycle stream. A controlled volume of reaction zone effluent can be recycled back to the front of the reaction zone, using a reheater as necessary, and blended with fresh feed and hydrogen. The recycle stream absorbs heat created by the reaction of the feed and hydrogen on the catalyst and reduces the temperature rise through the reaction zone. The reaction zone temperature can be controlled by controlling the fresh feed temperature, using a preheater as necessary, and the amount of recycle. In addition, because the recycle stream contains molecules that have already reacted, it also serves as an inert diluent, as previously discussed.

The use of a liquid phase reaction zone provides an additional level of control of the temperature inside the reaction zone. The advantage of a liquid phase reactor is that liquids, in general, have higher heat capacities than gases. The greater the heat capacity of a given material, the greater ability that material has for absorbing heat from its surroundings while undergoing a minimal increase in temperature itself. A liquid phase reactor acts as a heat sink, absorbing excess heat from the reaction zone to equalize the temperature throughout. With the introduction of the liquid phase reactor using typical hydroprocessing feedstocks, the process becomes much closer to being isothermal, reducing a typical 40° F. to 60° F. temperature difference between the reactor inlet and reactor outlet to approximately a 5° F. to 15° F. temperature difference. In addition to reducing the temperature difference between the reactor inlet and reactor outlet temperatures, the liquid phase reactor also serves to greatly reduce the problem of hot spots developing within the catalyst bed. Consequently, with the use of liquid phase hydroprocessing according to the present invention, coking can be nearly eliminated or minimized because there is always enough hydrogen available in solution to avoid coking when cracking reactions take place. This can lead to much longer catalyst life and reduced operating and maintenance costs.

While conventional hydroprocessing of typical hydrocarbon feedstocks may generate heat, the amount of heat generated in these reactions is insignificant compared to the heat generated during the hydroproces sing of highly contaminated and/or highly olefinic feedstocks, as described herein. These feedstocks, whether a hydrocarbon feedstock or a biological or renewable feedstock, require massive amounts of hydrogen. Consequently, hydroprocessing of these materials creates significantly more heat than can be managed using a conventional hydroprocessing process. To create quality products from these high-contaminant and/or high-olefinic feedstocks and to maintain catalyst activity and integrity, more must be done to remove heat and control the temperature of the process.

The extreme quantities of heat can be managed by keeping reaction zones small and utilizing multiple reaction zones to accomplish the goal, by providing an adequate quantity of liquid diluent or recycle to increase the heat capacity of the liquids inside the reaction zone(s), and by providing a method of removing heat from the liquid reactants between reaction zones using heat exchangers or flash vessels to lower the temperature of the liquid reactants prior to entry into subsequent reaction zones.

Another problem found in hydroprocessing is the production of reaction by-products, namely light end hydrocarbon gases. These molecules, predominately methane, are an undesirable product which, in great enough quantities, must be recovered, at additional cost. These light ends increase in quantity as the temperature of the reaction goes up. The problem of light end production is further compounded by the tendency for a reactor to develop hot spots, areas where the temperature increases significantly above the set temperature for the reactor. To combat this occurrence, conventional hydroprocessing systems employ the use of quench boxes which are placed throughout the reactor. The quench boxes serve to inject cold hydrogen into the reactor to reduce the temperature inside the reactor. Not only is hydrogen an expensive choice for cooling the reactor, it can pose a safety hazard. The design of the quench boxes and the method of controlling how they introduce hydrogen into the reactor are vital, because an error could cause the loss of control of the entire system. A runaway reaction could be started, possibly creating an explosion.

Using liquid phase hydroprocessing, cracking is greatly reduced, often by a 10-fold reduction, through the use of a liquid phase reactor working also as a heat sink to create a reactor environment that is close to isothermal. The amounts of light end hydrocarbons are therefore significantly reduced. This near isothermal environment eliminates the need for cold hydrogen quench boxes, reduces the capital cost of hydrogen required for the process and increases the safety of the system.

In the hydroprocessing of high-contaminant and/or high-olefinic feedstocks, especially those of biological origin, the reaction by-products produced during hydroproces sing are a serious concern. Higher feedstock contaminant levels translate to greater quantities of reaction by-products from those contaminants: hydrogen sulfide, ammonia, sulfur, carbon, and, of perhaps greatest concern, water. In large enough quantities, these by-products can wreck havoc on catalyst beds. Indeed, depending on the oxygen content of the feed, water produced as a reaction product in the reactor or reactors may make up from at least 10%, 20%, 30%, 40%, 50% or more by weight of the reaction products produced in such reactor or reactors. Water, specifically, has the potential to come out of solution with the hydrocarbonaceous reactants and products. If this occurs, wherein two separate liquid phases, i.e. an aqueous phase and a hydrocarbonacous phase, are present in the reaction zone, the aqueous phase will rapidly deactivate the catalyst and may effectively dissolve it inside the reactor.

The buildup of hydrogen sulfide and ammonia are also of great concern, as they are both widely known to inhibit catalyst activity. With the hydroprocessing of high-contaminant and/or high-olefinic feedstocks, the production of these undesirable reaction by-products may occur at levels to cause concern. In order to create quality products from these high-contaminant and/or high-olefinic feedstocks and maintain catalyst activity and integrity, the quantities of these reaction by-products in solution must be controlled so as to prevent their build-up to levels that will compromise the process.

The combination of controlling reaction zone temperature and managing the quantity of harmful reaction by-products in the process: utilizing multiple small reaction zones, providing an adequate quantity of a diluent or recycle to increase the capacity of the liquids inside the reaction zone for holding heat and keeping reaction by-products in solution, and the use of heat exchangers, separators, and/or flash vessels to remove undesirable quantities of heat and reaction by-products from the liquid reactants prior to entry into subsequent reaction zones, all facilitate making the hydroprocessing of highly contaminated and/or highly olefinic feedstocks a viable option.

Referring to FIG. 1, a flow diagram schematic of a hydroprocessing system 100 that is configured in accordance with the invention is shown. A high-contaminant and/or high-olefinic feedstock 101, which may be a renewable material, such as pyrolysis oil or those non-petroleum materials previously described, is passed through preheater 102. Preheater 102 may only be required during unit startup. After the initial startup period, the feedstock 101 is preheated as it passes through a series of heat exchangers: 115, 135, 155, 175, and 195, and preheater 102 is no longer necessary. The heated high-contaminant and/or high-olefinic feedstock 101 is then blended with a diluent 103 to form a liquid feedstock-diluent mixture 104. The amount of diluent 103 added may be that sufficient to dissolve a preselected amount of hydrogen in the combined feed-diluent mixture; to maintain the temperature within the reactor(s) below a preselected temperature; or to adjust the capacity of the liquid phase to dissolve or carry water; or a combination of these.

A controlled amount of hydrogen gas 105 is mixed with and dissolved into feedstock-diluent mixture 104 to form a liquid phase feed, diluent, and hydrogen mixture 109.

The liquid feedstock, diluent, and hydrogen mixture 109 is then fed into reactor 110 and reacted in the reactor's reaction zone(s) to form a liquid phase reacted effluent 112 containing reaction products. Any evolved or excess undissolved hydrogen gas and light ends may be vented from the top of the reaction zone(s) through vent 113 to facilitate controlling the quantity of liquids in the reactor. In other embodiments, hydrogen gas remains in the reactor(s) with no venting of hydrogen gas from the reactor(s). Alternatively, any venting of hydrogen gas from the reactor may be for purposes other than for controlling the quantity of liquid within the reactor, with the liquid level within reactor 110 being controlled by the input of hydrogen at 105.

The reacted effluent 112 is then passed through heat exchanger 115 to lower the temperature of the reacted effluent 112 and to facilitate the separation of light end hydrocarbons, water, other reaction by-products, and excess hydrogen from the reacted effluent 112 into the gas phase to create multi-phase reacted effluent 117 comprising: 1) a gas phase reacted effluent and a liquid phase hydrocarbonaceous reacted effluent or 2) a gas phase reacted effluent, a liquid phase hydrocarbonaceous reacted effluent, and liquid water or aqueous phase. The multi-phase reacted effluent 117 is then introduced into separator 120 and separated into as many as three separate components: liquid water 122, hydrocarbonaceous reacted effluent 124, and gas phase reacted effluent 126 comprising light ends and excess hydrogen gas. The rate at which the gas phase reacted effluent 126 exits the separator 120 is controlled by valve 127. Note that, depending on the feedstock and process conditions, liquid water 122 may not be formed in the separator. If water is created as a reaction by-product in reactor 110, it may, alternately, remain dissolved in the hydrocarbonaceous phase of the reacted effluent 117 or it may also move into the gas phase as a vapor and exit the separator 120 with the gas phase reacted effluent 126.

Additional hydrogen gas 128 is then mixed with and dissolved into liquid hydrocarbonaceous reacted effluent 124 and fed into intermediate reactor 130 and reacted in the reactor's reaction zone(s) to form a liquid phase reacted effluent 132. Any excess undissolved hydrogen gas and light ends may be vented from the top of the reaction zone(s) through vent 133. The quantity of hydrogen gas 128 added to the hydrocarbonaceous reacted effluent 124 is adjusted by valve 129, which is controlled by level controller 131. The reacted effluent 132 is then passed through heat exchanger 135 to lower the temperature of the reacted effluent and to facilitate the separation of light end hydrocarbons, water, other reaction by-products, and excess hydrogen from the reacted effluent 132 into the gas phase to create multi-phase reacted effluent 137 comprising: 1) a gas phase reacted effluent and a liquid phase hydrocarbonaceous reacted effluent or 2) a gas phase reacted effluent, a liquid phase hydrocarbonaceous reacted effluent, and liquid water or aqueous phase. The multi-phase reacted effluent 137 is then introduced into separator 140 and separated into as many as three separate components: liquid water or aqueous phase 142, liquid hydrocarbonaceous reacted effluent 144, and gas phase reacted effluent 146. The rate at which the gas phase reacted effluent 146 exits the separator 140 is adjusted by valve 147.

Additional hydrogen gas 148 is then mixed with and dissolved into the liquid hydrocarbonaceous reacted effluent 144 and fed into intermediate reactor 150 and reacted in the reactor's reaction zone(s) to form a liquid phase reacted effluent 152. Excess undissolved hydrogen gas and light ends may be vented from the top of the reaction zone(s) through vent 153. The quantity of hydrogen gas 148 added to the hydrocarbonaceous reacted effluent 144 is adjusted by valve 149, which is controlled by level controller 151. The reacted effluent 152 is then passed through heat exchanger 155 to lower the temperature of the reacted effluent and to facilitate the separation of light end hydrocarbons, water, other reaction by-products, and excess hydrogen from the reacted effluent 152 into the gas phase to create multi-phase reacted effluent 157 comprising: 1) a gas phase reacted effluent and a liquid phase hydrocarbonaceous reacted effluent or 2) a gas phase reacted effluent, a liquid phase hydrocarbonaceous reacted effluent, and liquid water or aqueous phase. The multi-phase reacted effluent 157 is then introduced into separator 160 and separated into as many as three separate components: liquid water or aqueous phase 162, liquid hydrocarbonaceous reacted effluent 164, and gas phase reacted effluent 166. The rate at which the gas phase reacted effluent 166 exits the separator 160 is adjusted by valve 167.

Additional hydrogen gas 168 is then mixed with and dissolved into the liquid hydrocarbonaceous reacted effluent 164 and fed into intermediate reactor 170 and reacted in the reactor's reaction zone(s) to form a liquid phase reacted effluent 172. Excess undissolved hydrogen gas and light ends are vented from the top of the reaction zone(s) through vent 173. The quantity of hydrogen gas 168 added to the hydrocarbonaceous reacted effluent 164 is adjusted by valve 169, which is controlled by level controller 171. The reacted effluent 172 is then passed through heat exchanger 175 to lower the temperature of the reacted effluent and to facilitate the separation of light end hydrocarbons, water, other reaction by-products, and excess hydrogen from the reacted effluent 172 into the gas phase to create multi-phase reacted effluent 177 comprising: 1) a gas phase reacted effluent and a liquid phase hydrocarbonaceous reacted effluent or 2) a gas phase reacted effluent, a liquid phase hydrocarbonaceous reacted effluent, and liquid water or aqueous phase. The multi-phase reacted effluent 177 is then introduced into separator 180 and separated into as many as three separate components: liquid water or aqueous phase 182, liquid hydrocarbonaceous reacted effluent 184, and gas phase reacted effluent 186. The rate at which the gas phase reacted effluent 186 exits the separator 180 is adjusted by valve 187.

Additional hydrogen gas 188 is then mixed with and dissolved into the liquid hydrocarbonaceous reacted effluent 184 and fed into a final reactor 190 and reacted in the reactor's reaction zone(s) to form a final liquid phase reacted effluent 192. Excess undissolved hydrogen gas and light ends may be vented from the top of the reaction zone(s) through vent 193. The quantity of hydrogen gas 188 added to the liquid hydrocarbonaceous reacted effluent 184 is adjusted by valve 189, which is controlled by level controller 191. The final reacted effluent 192 is then passed through heat exchanger 195 to lower the temperature of the reacted effluent 192 and to facilitate the separation of light end hydrocarbons, water, other reaction by-products, and excess hydrogen from the reacted effluent 192 into the gas phase to create multi-phase reacted effluent 197 comprising: 1) a gas phase reacted effluent and a liquid phase hydrocarbonaceous reacted effluent or 2) a gas phase reacted effluent, a liquid phase hydrocarbonaceous reacted effluent, and liquid water or aqueous phase. The multi-phase reacted effluent 197 is then introduced into separator 200 and separated into as many as three separate components: liquid water or aqueous phase 202, final liquid hydrocarbonaceous product 204, and gas phase reacted effluent 206.

A portion of final hydrocarbonaceous product 204 may then be used to form the diluent stream 103 that is mixed with the initial high-contaminant and/or high-olefinic feedstock 101 at the start of the process. Although not shown, the final product 204 or other intermediate liquid hydrocarbonaceous product streams may also be recycled and used as added diluent for any feedstream introduced into any of the initial or intermediate reactors to facilitate dissolution of hydrogen. Alternatively, diluent from another source may be mixed with the initial feedstock 101 or intermediate feed streams.

Figure 2:
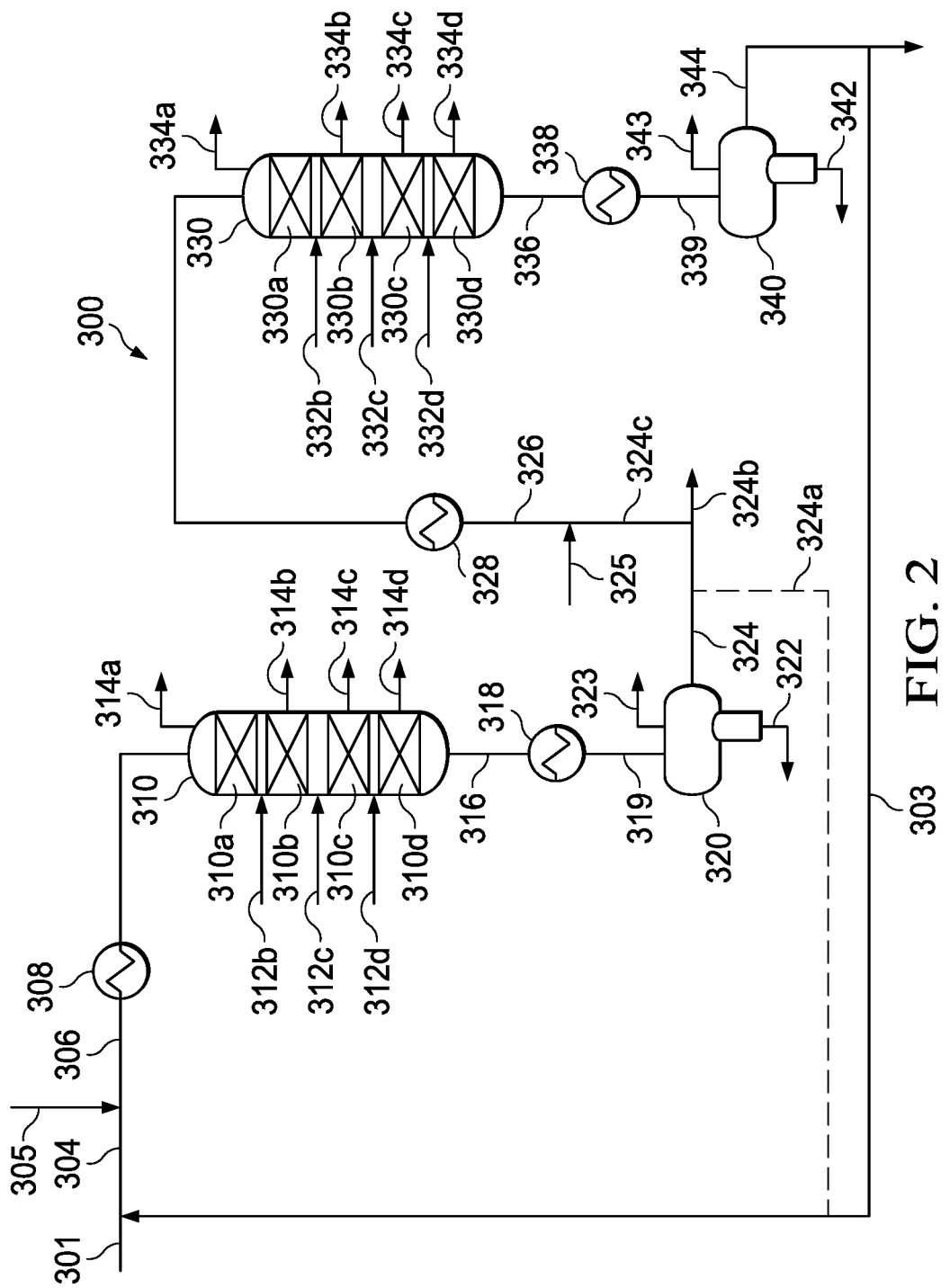
FIG. 2 is a process flow diagram schematic showing a hydroprocessing system that may be used for hydroprocessing of high-contaminant and/or high-olefinic feedstocks and that employs reactors having multiple reaction zones.

FIG. 2 shows a flow diagram schematic of another hydroprocessing system generally designated by the numeral 300. A high-contaminant and/or high-olefinic feedstock 301, which may be formed from those high-contaminant and/or high-olefinic feedstocks described herein, such as a non-petroleum, renewable material, such as pyrolysis oil, that contains high levels of oxygen (e.g. greater than 10% by weight) is treated in the system 300. The feedstock 301 is mixed with a liquid diluent 303 to form a liquid feedstock-diluent mixture 304. Hydrogen gas 305 is mixed with and dissolved in the liquid feedstock-diluent mixture 304 to form a liquid phase feedstock, diluent, and hydrogen mixture 306. The feedstock, diluent, and hydrogen mixture 306 is then passed through heat exchanger 308 to increase the temperature of the feedstock, diluent, and hydrogen mixture 306 and then fed into reactor 310, containing a plurality of reaction zones, shown here as 310a, 310b, 310c, and 310d, where the feedstock, diluent, and hydrogen mixture 306 is reacted to form reacted effluent 316.

Additional hydrogen gas may be supplied and dissolved in the reacting feedstock, diluent, and hydrogen mixture 306 in between reaction zones at hydrogen inputs 312b, 312c, and 312d. The top of each reaction zone 310a, 310b, 310c, and 310d may be vented by vents 314a, 314b, 314c, and 314d to remove excess undissolved hydrogen gas and light ends. In other embodiments, no such venting may occur. In embodiments where the feed has a high oxygen content, water is one of the reaction products. Reacted effluent 316, which contains water, is passed through heat exchanger 318 to lower the temperature of the reacted effluent 316 and to facilitate the separation of light end hydrocarbons, water, other reaction by-products, and excess hydrogen from the reacted effluent 316 into the gas phase to create multi-phase reacted effluent 319 comprising a gas phase reacted effluent, a liquid phase hydrocarbonaceous reacted effluent, and liquid water or aqueous phase.

The multi-phase reacted effluent 319 is then introduced into separator 320 and separated into three components: liquid water or aqueous phase 322, gas phase reacted effluent 323, and hydrocarbonaceous reacted effluent 324. Hydrocarbonaceous reacted effluent 324 is then split into multiple streams. Optionally, a first portion of hydrocarbonaceous reacted effluent 324 may be utilized as a secondary diluent stream 324a, which can be combined with diluent 303. A second portion of hydrocarbonaceous reacted effluent 324 can serve as a product stream 324b. A third portion of hydrocarbonaceous reacted effluent 324 is required for the continuation of the process and becomes reacted effluent portion 324c.

Hydrogen gas 325 is then mixed with and dissolved in reacted effluent portion 324c to form a liquid phase reacted effluent and hydrogen mixture 326. The reacted effluent and hydrogen mixture 326 is then passed through heat exchanger 328 to increase the temperature of the reacted effluent and hydrogen mixture 326 and then fed into reactor 330, containing a plurality of reaction zones, shown here as 330a, 330b, 330c, and 330d, where the feedstock, diluent, and hydrogen mixture 326 is reacted to form reacted effluent 336.

Additional hydrogen gas is supplied and dissolved in the reacting feedstock, diluent, and hydrogen mixture 326 in between reaction zones at hydrogen inputs 332b, 332c, and 332d. The top of each reaction zone 330a, 330b, 330c, and 330d may be vented by vents 334a, 334b, 334c, and 334d to remove excess undissolved hydrogen gas and light ends. In other embodiments, no such venting occurs. Reacted effluent 336 is then passed through heat exchanger 338 to lower the temperature of the reacted effluent 336 and to facilitate the separation of light end hydrocarbons, any water, other reaction by-products, and excess hydrogen from the reacted effluent 336 into the gas phase to create multi-phase reacted effluent 339 comprising a gas phase reacted effluent, a liquid phase hydrocarbonaceous reacted effluent, and any liquid water or aqueous phase.

The multi-phase reacted effluent 339 is then introduced into separator 340 and separated into three components: liquid water or aqueous phase 342, gas phase reacted effluent 343, and final hydrocarbonaceous product 344. A portion of the hydrocarbonaceous product 344 is used to form the diluent stream 303 that may be mixed with the initial high-contaminant and/or high-olefinic feedstock 301 as the start of the process. The amount of diluent 303 and/or 324a added may be that selected to dissolve a preselected amount of hydrogen gas in the combined feed-diluent mixture; to maintain the temperature within the reactor(s) below a preselected temperature; or to adjust the capacity of the liquid phase to dissolve or carry water; or a combination of these.

Figure 3:
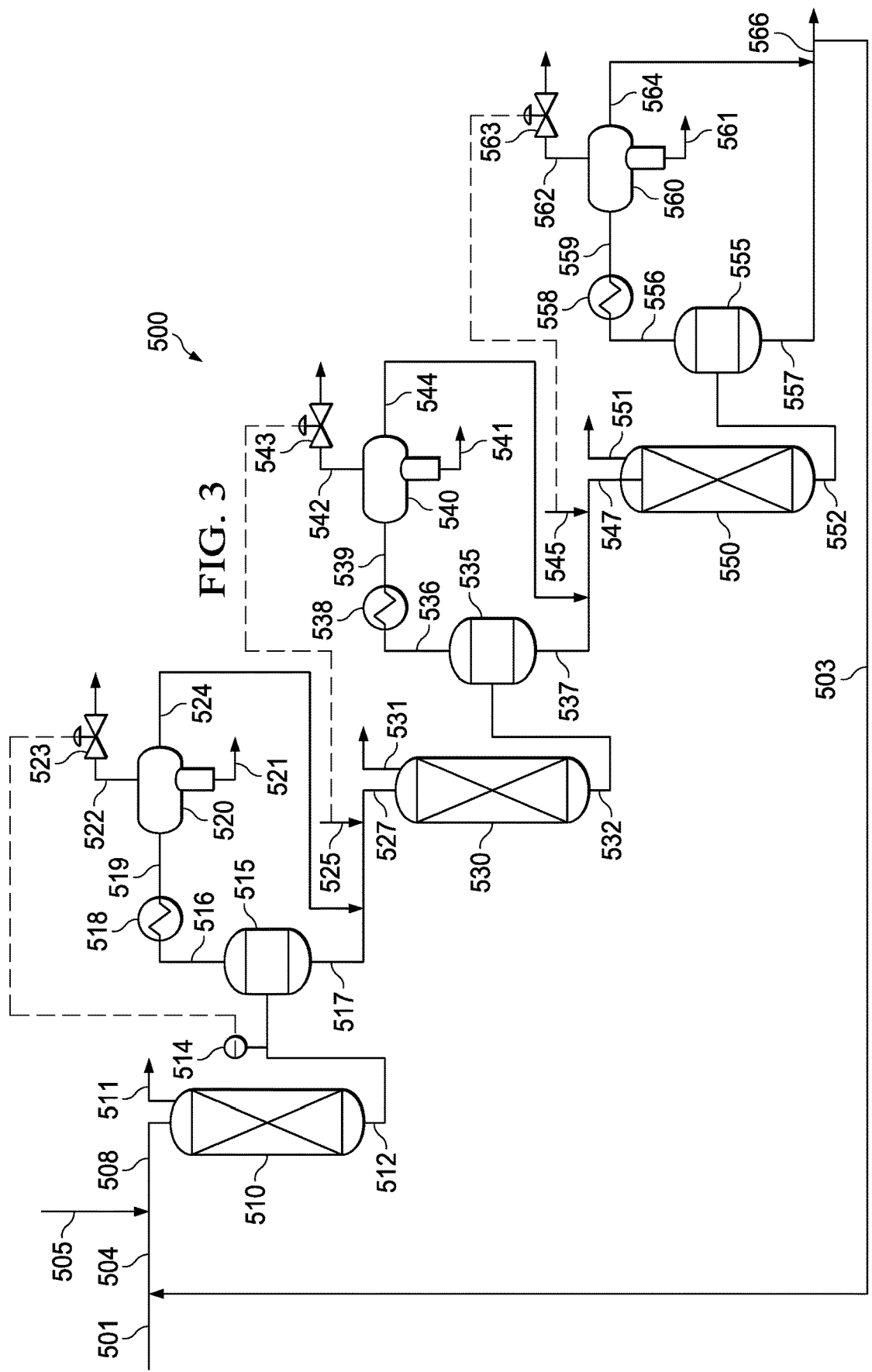
FIG. 3 is a process flow diagram schematic showing a hydroprocessing system employing flash vessels to facilitate separation of reaction products.

FIG. 3 shows another flow diagram schematic for a hydroprocessing system generally designated by the numeral 500. A high-contaminant and/or high-olefinic feedstock 501, such as those that have been described herein, is mixed with a liquid diluent 503 to form a liquid feedstock-diluent mixture 504. A controlled amount of hydrogen gas 505 is then mixed with and dissolved in the liquid feedstock-diluent mixture 304 to form a liquid phase feedstock, diluent, and hydrogen mixture 508.

The liquid feedstock, diluent, and hydrogen mixture 508 is then introduced into reactor 510 and reacted in the reactor's reaction zone(s) to form a liquid phase reacted effluent 512. Excess undissolved hydrogen gas and light ends 511 may be vented from the top of the reaction zone(s). In other embodiments, no venting of hydrogen gas from the reactor(s) occurs. Reacted effluent 512 then passes into flash vessel 515 where the reacted effluent 512 is split into two streams: a gas phase flash vessel effluent 516 and a liquid phase flash vessel effluent 517. The gas phase flash vessel effluent 516 is passed through a heat exchanger 518 to reduce the temperature of the gas phase flash vessel effluent 516 and to facilitate the condensation of a portion of the vapor phase flash vessel effluent 516 from the gas phase to the liquid phase and forming a multi-phase flash vessel effluent 519. The multi-phase flash vessel effluent is then introduced into a separator 520 and separated into three components: liquid water or aqueous phase 521, gas phase effluent 522, and liquid hydrocarbonaceous effluent 524. The quantity of gas phase effluent 522 exiting the separator 520 is adjusted by valve 523, which may serve to control the pressure in reactor 510 through pressure controller 514.

The liquid hydrocarbonaceous effluent 524 is then combined with the liquid phase flash vessel effluent 517 before being mixed with a controlled amount of hydrogen gas 525 to form a liquid phase intermediate feed 527. Intermediate feed 527 is then introduced into reactor 530 and reacted in the reactor's reaction zone(s) to form a liquid phase reacted effluent 532. Excess undissolved hydrogen gas and light ends 531 may be vented from the top of the reaction zone(s). In other embodiments, no such venting from the reactor occurs. Reacted effluent 532 then passes into flash vessel 535 where the reacted effluent 532 is split into two streams: a gas phase flash vessel effluent 536 and a liquid phase flash vessel effluent 537. The gas phase flash vessel effluent 536 is passed through a heat exchanger to reduce the temperature of the gas phase flash vessel effluent 536 and to facilitate the condensation of a portion of the vapor phase flash vessel effluent 536 from the gas phase to the liquid phase and forming a multi-phase flash vessel effluent 539.

The multi-phase flash vessel effluent is then introduced into a separator 540 and separated into three components: liquid water or aqueous phase 541, gas phase effluent 542, and liquid hydrocarbonaceous effluent 544. The quantity of gas phase effluent 542 exiting the separator 540 is adjusted by valve 543 which is used to control the quantity of additional hydrogen gas 525 added to the liquid phase flash vessel effluent 517 and the liquid hydrocarbonaceous effluent 524 prior to entry into reactor 530.

The liquid hydrocarbonaceous effluent 544 is then combined with the liquid phase flash vessel effluent 537 before being mixed with hydrogen gas 545 to form a liquid phase intermediate feed 547. Intermediate feed 547 is then introduced into reactor 550 and reacted in the reactor's reaction zone(s) to form a liquid phase reacted effluent 552. Excess undissolved hydrogen gas and light ends 551 may be vented from the top of the reaction zone(s). In other embodiments, no venting of the reactor occurs. Reacted effluent 552 then passes into flash vessel 555 where the reacted effluent 552 is split into two streams: a gas phase flash vessel effluent 556 and a liquid phase flash vessel effluent 557. The gas phase flash vessel effluent 556 is passed through a heat exchanger to reduce the temperature of the gas phase flash vessel effluent 556 and to facilitate the condensation of a portion of the vapor phase flash vessel effluent 556 from the gas phase to the liquid phase and forming a multi-phase flash vessel effluent 559.

The multi-phase flash vessel effluent is then introduced into a separator 560 and separated into three components: liquid water or aqueous phase 561, gas phase effluent 562, and liquid hydrocarbonaceous effluent 564. The quantity of gas phase effluent 562 exiting the separator 560 is adjusted by valve 563, which is used to control the quantity of additional hydrogen gas 545 added to the liquid phase flash vessel effluent 537 and the liquid hydrocarbonaceous effluent 544 prior to entry into reactor 550. The liquid hydrocarbonaceous effluent 564 is then combined with the liquid phase flash vessel effluent 557 to form a final product stream 566. A portion of the final product stream 566 may then be used to form the diluent stream 503 that is mixed with high-contaminant and/or high-olefinic feedstock 501 at the start of the process. The amount of diluent 503 added may be that sufficient to dissolve a preselected amount of hydrogen in the combined feed-diluent mixture; to maintain the temperature within the reactor(s) below a preselected temperature; or to adjust the capacity of the liquid phase to dissolve or carry water; or a combination of any of these.

Figure 4:
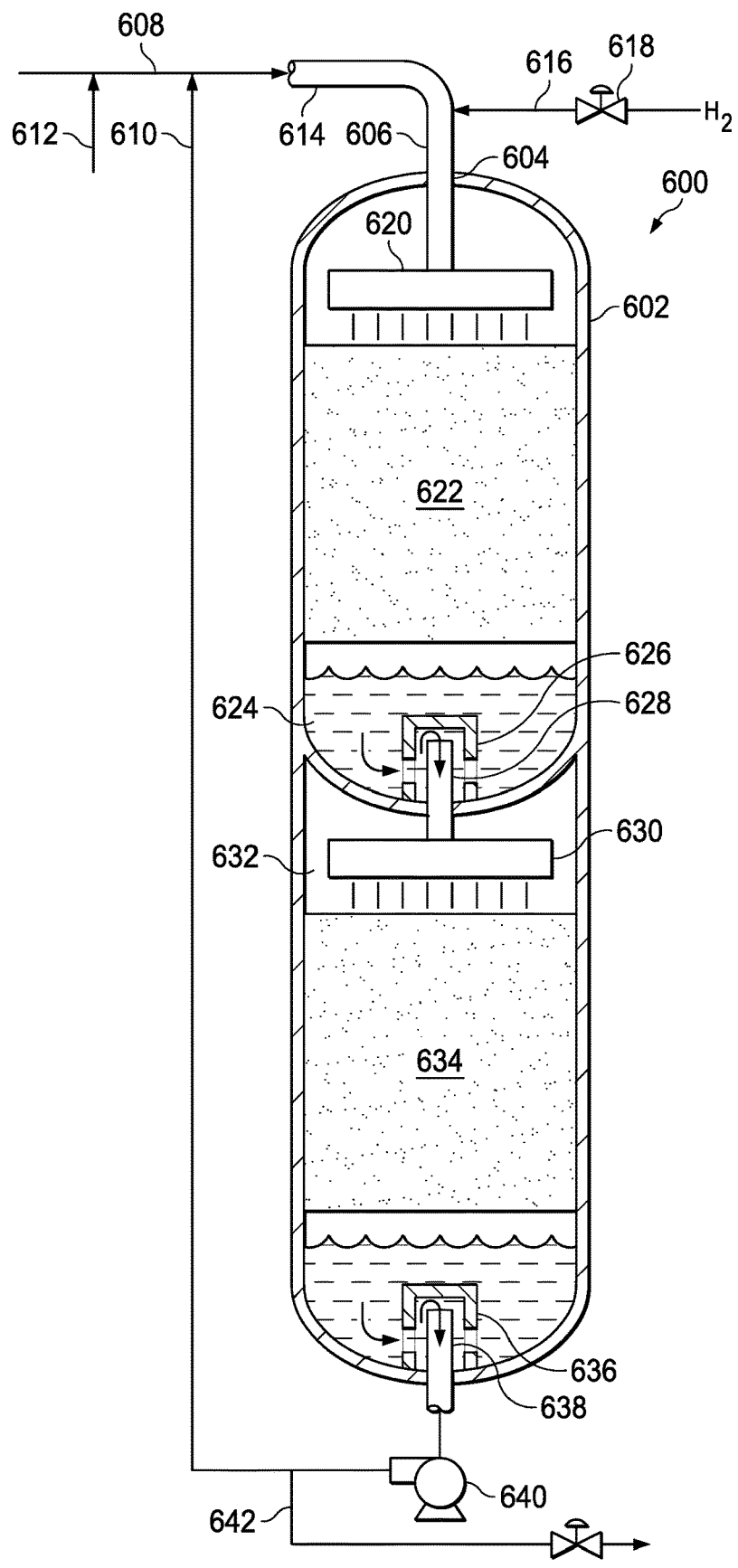
FIG. 4 is a schematic representation of a reactor that may be used in the hydroprocessing system for hydroprocessing high-contaminant and/or high-olefinic feedstocks.

FIG. 4 shows an example of a reactor 600 that may be used in any of the systems described herein. The reactor 600 includes a reactor vessel 602 that houses the various internal components of the reactor. The reactor 600 is provided with an inlet 604 at the upper end that is fluidly coupled to a feed line 606. The feed line 606 combines liquid feed 608, which may be a high-contaminant and/or high-olefinic non-petroleum liquid feed to be treated, with diluent or recycle feeds 610 and/or 612. The feed/diluent mixture is passed through line 614 where hydrogen gas is added to the feed/diluent mixture through line 616. The amount of hydrogen gas added is controlled by control valve 618 that is coupled to a hydrogen gas source.

The feed/diluent/hydrogen mixture is introduced into the reactor inlet 604 from feed line 606. The feed mixture is in a liquid phase, which may be a continuous liquid phase. The inlet 604 is fluidly coupled to a distributor 620. The liquid feed/diluent/hydrogen mixture is passed through the distributor 620 to catalyst bed 622 of an upper first reaction zone 624 containing a hydroprocessing catalyst. Hydrogen gas, which may be excess hydrogen gas, may also be passed through the distributor 620, and be present within the reactor vessel 602. The distributor 620 distributes the liquid feed/diluent/hydrogen over the catalyst bed 622. The feed mixture from the distributor 620 is passed as a liquid "bubbling feed" that may be in the form of a liquid stream or streams, which may or may not contain hydrogen gas, that is distributed over the catalyst bed 622 and should be distinguished from a conventional trickle bed reactor processes wherein large amounts of hydrogen gas are circulated through the catalyst bed.

Reacted liquid 624 is collected in the bottom of the reaction zone 622. The reacted liquid 624 is passed through outlet collector assembly 626 having an outlet conduit 628 that is fluidly coupled to a distributor 630 of a lower second reaction zone 632. The effluent from reaction zone 624 is passed from distributor 630 to second catalyst bed 634, which may contain the same or a different hydroprocessing catalyst from that of catalyst bed 622.

The reacted liquid of reaction zone 632 is collected at the bottom of the reactor 600 and is passed to outlet collector 636 to outlet conduit 638 and out of the reactor 600. This effluent is passed from conduit 638 to pump 640. All or a portion of the effluent from pump 640 may be passed through line 642 for further processing or as product. A portion may also be used as diluent as recycle 610. The diluents 612 may be a separate diluent source or a recycle from a different part of the system in which the reactor 600 is utilized.

While the reactor 600 is shown with two reaction zones, it may be also be configured to have a single reaction zone or three or more as well. Furthermore, the reactor 600 may be modified so that liquid collected from the upper reaction zone 624 is removed from the reactor through an outlet (not shown) and introduced into a separator and/or heat exchanger (not shown) where it may be flashed, cooled, and/or separated into different products (e.g. gases, hydrocarbons, water, etc.). The liquid product to be treated may then be reintroduced into the second reaction zone 632 through an inlet (not shown). Where more than two reaction zones exist in the reactor, such removal and reintroduction may occur with one or more of each of the reaction zones. Hydrogen and additional diluents may also be added to the reintroduced liquid between each reaction zone.

The following examples better serve to illustrate the invention.

EXAMPLES

Example 1

A pyrolysis oil derived from waste wood was hydrotreated in a system having two reaction zones, each containing a hydroprocessing catalyst. The pyrolysis oil had a specific gravity of 1.25, a sulfur content of 0.35% by weight, a nitrogen content of 0.28% by weight and an oxygen content of 35% by weight. Hydrogen gas was added to each the feeds prior to introduction into the reaction zones so that sufficient hydrogen necessary for the reaction was dissolved in the feeds introduced as a liquid phase. The reaction products were removed from each zone and cooled to 280° F. after each reaction zone. Water was removed from each of the cooled reaction products from each reaction zone. Approximately 40% of the water was removed after the first reaction zone and 60% was removed after the second reaction zone. All of the liquid reaction product from the first reaction zone with the water removed was used as the feed for the second reaction zone. Approximately 85% of the liquid reaction product from the second reaction zone with the water removed was used as a recycle ahead of the first reaction zone. Approximately 60% of the hydrogen was added to the first reaction zone and 40% of the hydrogen was added to the second reaction zone. In both cases the hydrogen addition was at a 10% excess above the solubility limit of the reaction zone feed mixture. The startup diluent used was a hydrocarbon similar to the water-free reaction product from the second reaction zone.

The reaction conditions in each reaction zone were as set forth in Table 1 below:

TABLE 1

| | |
|---|---|
| Pressure | 1850 psig |
| Reactor Weighted Ave. Bed Temp. (WABT) | 650° F. |
| Catalyst Volume | LHSV hr$^{-1}$: 3 |
| Recycle Ratio (weight basis)-Recycle to Feed | 5 to 1 |
| Hydrogen Addition to Feed | 4200 SCF/BB1 feed |

The following products, as set forth in Table 2 below, were obtained from the treatment:

TABLE 2

| Product | Amount |
|---|---|
| Light Ends (H$_2$S, NH$_3$, light hydrocarbons) | 15 wt. % of feed oil |
| Naptha | 35 wt. % of feed oil |
| Diesel | 15 wt. % of feed oil |
| Heavy Ends | 3 wt. % of feed oil |
| Water | 35 wt. % of feed oil |
| Total | 103 wt. % of feed oil |

Example 2

A pyrolysis oil derived from waste wood was hydrotreated in a system having a single reaction zone containing a hydroprocessing catalyst. The pyrolysis oil had a specific gravity of 1.25, a sulfur content of 0.35% by weight, a nitrogen content of 0.28% by weight and an oxygen content of 35% by weight. Hydrogen gas was added to the feed prior to introduction into the reaction zone so that sufficient hydrogen necessary for the reaction was dissolved in the feed introduced as a liquid phase. The reaction products were removed from the reaction zone and cooled to 280° F. Water at 100% was removed from the cooled reaction products. Approximately 95% of the reaction product with the water removed was used as a recycle ahead of the reaction zone. All of the hydrogen was added to the reaction zone at a 10% excess above the solubility limit of the feed mixture. The startup diluent used was a hydrocarbon similar to the water-free reaction product.

The reaction conditions in the reaction zone were as set forth in Table 3 below:

TABLE 3

| | |
|---|---|
| Pressure | 2055 psig |
| Reactor Weighted Ave. Bed Temp. (WABT) | 660° F. |
| Catalyst Volume | LHSV hr$^{-1}$: 2 |
| Recycle Ratio (weight basis)-Recycle to Feed | 11 to 1 |
| Hydrogen Addition to Feed | 4700 SCF/BB1 feed |

The following products, as set forth in Table 4 below, were obtained from the treatment:

TABLE 4

| Product | Amount |
|---|---|
| Light Ends (H$_2$S, NH$_3$, light hydrocarbons) | 13 wt. % of feed oil |
| Naptha | 37 wt. % of feed oil |
| Diesel | 14 wt. % of feed oil |
| Heavy Ends | 5 wt. % of feed oil |
| Water | 35 wt. % of feed oil |
| Total | 104 wt. % of feed oil |

Example 3

A pyrolysis oil derived from waste wood was hydrotreated in a system having two reaction zones containing a hydroprocessing catalyst. The pyrolysis oil had a specific gravity of 1.25, a sulfur content of 0.35% by weight, a nitrogen content of 0.28% by weight and an oxygen content of 35% by weight. Hydrogen gas was added to the feeds prior to introduction into the reaction zones so that sufficient hydrogen necessary for the reaction was dissolved in the feeds and introduced as a liquid phase. The reaction products were removed from each zone and cooled to 280° F. after each reaction zone. Water was removed from each of the cooled reaction products from each reaction zone. Approximately 40% of the water was removed after the first reaction zone and 60% was removed after the second reaction zone. All of the liquid reaction product from the first reaction zone with the water removed was used as the feed for the second reaction zone. Approximately 85% of the liquid reaction product from the second reaction zone with the water removed was used as a recycle ahead of the first reaction zone. Approximately 60% of the hydrogen was added to the first reaction zone and 40% of the hydrogen was added to the second reaction zone. In both cases the hydrogen addition was at a 10% excess above the solubility limit of the feed mixture. The startup diluent used was a hydrocarbon similar to the water-free reaction product from the second reaction zone.

The reaction conditions in each reaction zone were as set forth in Table 5 below:

TABLE 5

| | |
|---|---|
| Pressure | 1100 psig |
| Reactor Weighted Ave. Bed Temp. (WABT) | 680° F. |
| Catalyst Volume | LHSV hr$^{-1}$: 1.5 |
| Recycle Ratio (weight basis)-Recycle to Feed | 10 to 1 |
| Hydrogen Addition to Feed | 3900 SCF/BB1 feed |

The following products, as set forth in Table 6 below, were obtained from the treatment:

TABLE 6

| Product | Amount |
|---|---|
| Light Ends ($H_2S$, $NH_3$, light hydrocarbons) | 14 wt. % of feed oil |
| Naptha | 30 wt. % of feed oil |
| Diesel | 16 wt. % of feed oil |
| Heavy Ends | 8 wt. % of feed oil |
| Water | 35 wt. % of feed oil |
| Total | 103 wt. % of feed oil |

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of hydroprocesing comprising:
   (a) introducing a non-petroleum feed to be treated along with a diluent and hydrogen into a first reaction zone containing a hydroprocessing catalyst, the amount of diluent combined with the non-petroleum feed being selected to at least one of (A) dissolve a preselected amount of hydrogen in the combined non-petroleum/diluent feed; (B) maintain the temperature within the reactor below a preselected temperature; and (C) adjust the capacity of the liquid phase to dissolve or carry water hydrogen;
   (b) allowing the feed and hydrogen to react in a liquid phase within the first reaction zone to produce reaction products, at least one of the reaction products being water;
   (c) removing the reaction products from the first reaction zone;
   (d) separating water from the removed reaction products as an aqueous phase to provide a separated reaction product that is free from the separated water; and
   (e) introducing at least a portion of the separated reaction product as a feed along with hydrogen into a second reaction zone containing a hydroprocessing catalyst; and
   (f) allowing the separated reaction product feed and hydrogen to react in a liquid phase within the second reaction zone to produce a second-reaction-zone reaction product.

2. The method of claim 1, wherein:
the diluent is provided by at least one of (1) a further portion of the separated reaction product of step (d) and (2) at least a portion of the second-reaction-zone reaction product of step (f).

3. The method of claim 1, wherein:
the separated reaction product is substantially water-free.

4. The method of claim 1, wherein:
water makes up at least 10% by weight of the total reaction products.

5. The method of claim 1, wherein:
the non-petroleum feed is comprised of pyrolysis oils.

6. The method of claim 5, wherein:
the pyrolysis oils are derived from at least one of cellulosic biomass materials and coal.

7. The method of claim 1, wherein:
the non-petroleum feed is at least one of vegetable oil and animal oil.

8. The method of claim 1, wherein:
the non-petroleum feed is introduced in the first reaction zone under conditions so that substantially all the feed and hydrogen are in a continuous liquid phase within the first reaction zone.

9. The method of claim 1, wherein:
the removed reaction products of step (c) are cooled prior to separating water according to (d).

10. The method of claim 1, wherein:
the first and second reaction zones are reactors and wherein each reactor contains greater than 10% hydrogen gas by total volume of the reactor.

11. The method of claim 1, wherein:
no excess hydrogen gas is vented from the first and second reaction zones to facilitate controlling quantities of liquids within the reaction zones.

12. A method of hydroprocesing comprising:
   (a) introducing a non-petroleum feed to be treated along with a diluent and hydrogen into a first reaction zone containing a hydroprocessing catalyst, the amount of diluent combined with the non-petroleum feed being selected to at least one of (A) dissolve a preselected amount of hydrogen in the combined non-petroleum/diluent feed; (B) maintain the temperature within the reactor below a preselected temperature; and (C) adjust the capacity of the liquid phase to dissolve or carry water;
   (b) allowing the feed and hydrogen to react in a liquid phase within the first reaction zone to produce reaction products, at least one of the reaction products being water;
   (c) removing the reaction products from the first reaction zone;
   (d) cooling the removed reaction products;
   (e) separating water from the removed reaction products to provide a separated reaction product that is free from the separated water;
   (f) introducing at least a portion of the separated reaction product as a feed along with hydrogen into a second reaction zone containing a hydroprocessing catalyst;
   (g) allowing the separated reaction products and hydrogen to react in a liquid phase within the second reaction zone to produce reaction products;
   (h) removing the reaction products produced in (g) from the second reaction zone;
   (i) cooling the removed reaction products from (h); and
   (j) separating any gas phase and any liquid water phase from the cooled reaction products from (i) to form a separated reaction product that is free from any separated liquid water to provided a separated liquid reaction product.

13. The method of claim 12, wherein:
the diluent is provided by at least one of (1) a further portion of the separated reaction product of step (e) and (2) at least a portion of the separated liquid reaction product of step (j).

14. The method of claim 12, wherein:
the separated reaction products of steps (e) and (j) are substantially water-free.

15. The method of claim 12, wherein:
water makes up at least 10% by weight of the total reaction products.

16. The method of claim 12, wherein:
the non-petroleum feed is comprised of pyrolysis oils.

17. The method of claim 16, wherein:
the pyrolysis oils are derived from at least one of cellulosic biomass materials and coal.

18. A method of hydroprocessing comprising:
(a) introducing a non-petroleum feed to be treated containing at least one of olefinic compounds and heteroatom contaminants along with a diluent and hydrogen into a first reaction zone containing a hydroprocessing catalyst, the amount of diluent combined with the non-petroleum feed being selected to at least one of (A) dissolve a preselected amount of hydrogen in the combined non-petroleum/diluent feed; (B) maintain the temperature within the reactor below a preselected temperature; and (C) adjust the capacity of the liquid phase to dissolve or carry water;
(b) allowing the feed and hydrogen to react in a liquid phase within the first reaction zone to produce reaction products;
(c) removing the reaction products from the first reaction zone;
(d) cooling the removed reaction product;
(e) introducing at least a portion of the cooled reaction product as a feed along with hydrogen into a second reaction zone containing a hydroprocessing catalyst; and
(f) allowing the cooled reaction product and hydrogen to react in a liquid phase within the second reaction zone to produce a second-reaction-zone reaction product.

19. The method of claim 18, wherein:
the diluent is provided by at least one of (1) a further portion of the cooled reaction product of step (d) and (2) at least a portion of the second-reaction-zone reaction product of step (f).

20. The method of claim 18, further comprising:
separating any water from the cooled reaction products of steps (d) and (f) as an aqueous phase to provide separated reaction products that are free from the separated water; and wherein
the diluent is provided by at least a portion of one of the separated reaction products from steps (d) and (f).

* * * * *

UNITED STATES PATENT AND TRADEMARK OFFICE
CERTIFICATE OF CORRECTION

PATENT NO. : 10,961,463 B2  
APPLICATION NO. : 16/694602  
DATED : March 30, 2021  
INVENTOR(S) : Michael D. Ackerson and Michael Steven Byars Page 1 of 1

It is certified that error appears in the above-identified patent and that said Letters Patent is hereby corrected as shown below:

In the Claims

At Column 17, Line 40, please replace "hydroproces sing" with --hydroprocessing--.

At Column 17, Line 50, please delete the word "hydrogen.".

At Column 18, Line 36, please replace "hydroproces sing" with --hydroprocessing--.

At Column 19, Line 2, please replace "provided" with --provide--.

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*